United States Patent
Rousseau et al.

(10) Patent No.: US 6,812,347 B2
(45) Date of Patent: Nov. 2, 2004

(54) PROCESSES FOR THE PREPARATION OF PESTICIDAL COMPOUNDS AND NOVEL INTERMEDIATES THEREOF

(75) Inventors: Jean-François Rousseau, Saint-Drezery (FR); Albert Buforn, Lyons (FR)

(73) Assignee: Bayer Cropscience S.A., Lyons (FR)

( * ) Notice: Subject to any disclaimer, the term of this patent is extended or adjusted under 35 U.S.C. 154(b) by 0 days.

(21) Appl. No.: 10/297,675

(22) PCT Filed: Jun. 7, 2001

(86) PCT No.: PCT/EP01/07399

§ 371 (c)(1),
(2), (4) Date: Apr. 30, 2003

(87) PCT Pub. No.: WO01/94316

PCT Pub. Date: Dec. 13, 2001

(65) Prior Publication Data

US 2003/0166940 A1 Sep. 4, 2003

Related U.S. Application Data
(60) Provisional application No. 60/210,803, filed on Jun. 9, 2000.

(30) Foreign Application Priority Data

Jan. 16, 2001 (EP) .............................................. 0100893

(51) Int. Cl.[7] ..................... C07D 401/04; C07D 231/40
(52) U.S. Cl. .................. 546/276.1; 548/368.4
(58) Field of Search ...................... 546/276.1; 548/368.4

(56) References Cited

U.S. PATENT DOCUMENTS

| | | |
|---|---|---|
| 4,931,461 A | 6/1990 | Jensen-Korte et al. |
| 5,556,873 A | 9/1996 | Huang et al. |
| 6,160,002 A | 12/2000 | Huber et al. |

FOREIGN PATENT DOCUMENTS

WO 00/35884 A1 6/2000

OTHER PUBLICATIONS

Cram and Hammond, "Organic Chemistry", McGraw Hill Book Co., NY (1964) 2nd Ed., pp 565–67.*

* cited by examiner

Primary Examiner—Patricia L. Morris
(74) Attorney, Agent, or Firm—Burns, Doane, Swecker & Mathis, L.L.P.

(57) ABSTRACT

A process for the preparation of a compound of the formula (I):

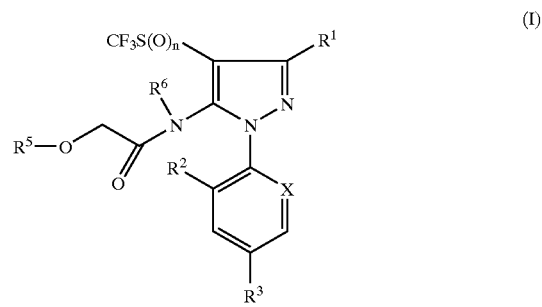

wherein $R^1$ is CN or $CSNH_2$; X is N or $CR^4$; $R^2$ and $R^4$ are each independently hydrogen or chloro; $R^3$ is halo, haloalkyl, haloalkoxy or $-SF_5$; $R^5$ and $R^6$ are each independently alkyl and n is 0, 1 or 2; said process comprising reacting a compound of the formula (II):

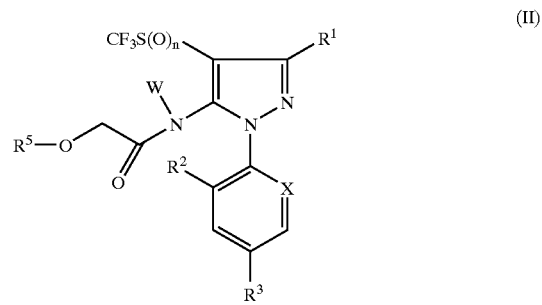

wherein the symbols are as defined above and W is H, with an alkylating agent of the formula (III):

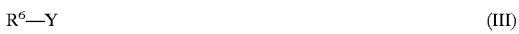

wherein $R^6$ is as defined above and Y is a leaving group. The process may also be conducted by reacting a compound of formula (II) initially with an inorganic salt or an organic base, and reacting the resultant salt of the compound of formula (II) with the alkylating agent.

37 Claims, No Drawings

PROCESSES FOR THE PREPARATION OF PESTICIDAL COMPOUNDS AND NOVEL INTERMEDIATES THEREOF

This application claims the benefit of U.S. Provisional Patent Application No. 60/210,803, filed Jun. 9, 2000.

FIELD OF THE INVENTION

The present invention relates to a process for the preparation of substituted pyrazoles and to their use as pesticidal compounds.

BACKGROUND OF THE PRIOR ART

Pyrazoles such as 5-amino-1-aryl-3-cyanopyrazole compounds and derivatives thereof, for example fipronil, form an important class of insecticides. Certain substituted 5-N-alkyl-N-alkoxyacetylamino-1-aryl-3-cyanopyrazole compounds also have valuable pesticidal properties, as disclosed in WO00/35884 and U.S. Pat. No. 5,556,873.

U.S. Pat. No. 4,931,461 discloses substituted 5-methylamino-1-aryl pyrazoles and their use as pest-combating agents. These substituted compounds may be prepared in various ways, but in particular it has been found that the compounds may be prepared by reacting the pyrazole with an alkylating agent. This preparation method, while being effective, produces by-products that must be isolated from the desired pesticidal compound.

We have found an alternative route to the production of the aforementioned compounds which reduces and substantially eliminates the presence of by-products, thus avoiding the need to purify the final product.

SUMMARY OF THE INVENTION

Accordingly, the present invention provides a process (A) for the preparation of a compound of the formula (I):

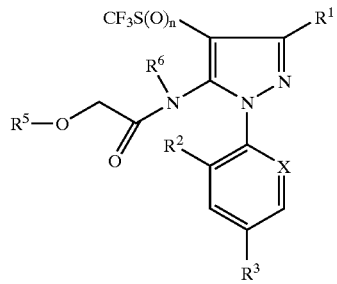

wherein:
R$^1$ is CN or CSNH$_2$;
X is N or CR$^4$;
R$^2$ and R$^4$ are each independently hydrogen or chloro;
R$^3$ is halo, haloalkyl, haloalkoxy or —SF$_5$;
R$^5$ and R$^6$ are each independently alkyl; and
n is 0, 1 or 2;
which process comprises reacting a compound of the formula (II):

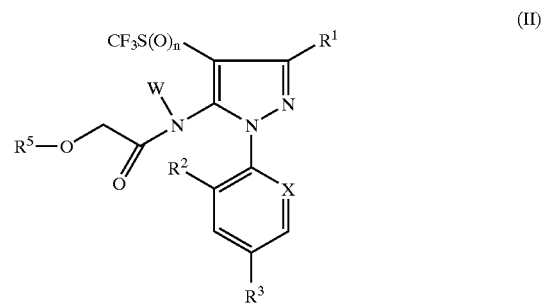

wherein the various symbols are as defined above and W is H, with an alkylating agent of the formula (III):

$$R^6—Y \qquad (III)$$

wherein R$^6$ is as defined above and Y is a leaving group.

This process provides the advantage over previously known processes in that this process is more efficient and provides a more direct route to the final product.

It has also been found that, prior to reacting compound (II) with the alkylating agent, compound (II) may be reacted initially with an inorganic metal salt or an organic base, thereby forming an intermediate salt which is then reacted with the alkylating agent.

Thus, according to a second aspect of the present invention there is provided a process (A) for the preparation of a compound of the formula (I)

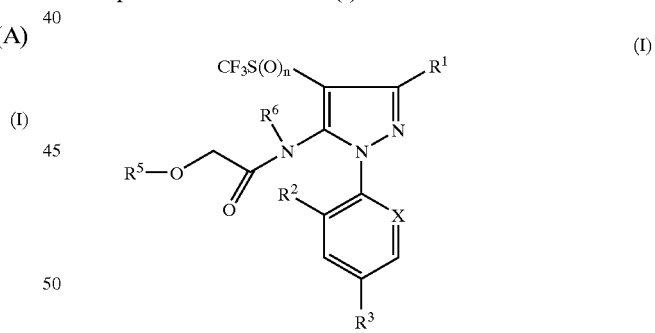

wherein:
R$^1$ is CN or CSNH$_2$;
X is N or CR$^4$;
R$^2$ and R$^4$ are each independently hydrogen or chloro;
R$^3$ is halo, haloalkyl, haloalkoxy or —SF$_5$;
R$^5$ and R$^6$ are each independently alkyl; and
n is 0, or 2;
which process comprises (a) a first step of reacting a compound of the formula (II):

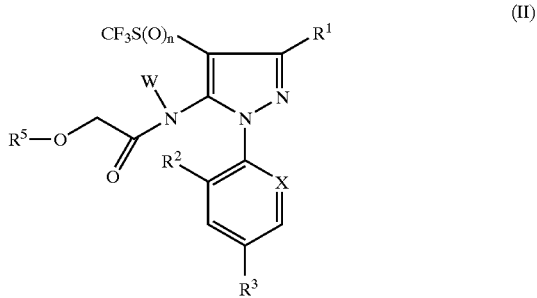

(II)

wherein the various symbols are as defined above and W is H, with an inorganic metal salt or an organic base to produce, as an intermediate compound, a salt of said compound of formula (II); and (b) a second step of reacting said salt of said compound of formula (II) with an alkylating agent of the formula (III):

$R^6$—Y (III)

wherein $R^6$ is as defined above and Y is a leaving group.

DETAILED DESCRIPTION OF THE INVENTION

The process of the present invention provides the advantage over the prior art in that there are no by-products produced during the reaction and that, if desired, the intermediate compound may be prepared and isolated. The intermediate compound has been found to be stable.

Furthermore, the intermediate compound obtained by the aforementioned process is a novel compound and hereby provides another aspect of the present invention.

The process of the present invention comprises reacting a compound of the formula (II) with an alkylating agent or, optionally, first with an inorganic salt or organic base, followed by the alkylating agent. With regard to $R^3$ of Compound (II), this group may be halo, haloalkyl, haloalkoxy or —$SF_5$. Suitable haloalkyls are halomethyls, especially trifluoromethyl. When $R^3$ is haloalkoxy, suitable haloalkoxy groups include halomethoxy, in particular trifluoromethoxy. With regard to $R^5$, this group is an alkyl group, for example methyl, ethyl or propyl, especially ethyl.

Preferably, the compound of the formula (II) has the following representations:

$R^1$ is CN;
X is $CR^4$;
$R^2$ and $R^4$ are each chlorine;
$R^3$ is trifluoromethyl;
$R^5$ is ethyl;
W is H; and
n is 1.

When the compound of the formula (II) is reacted with the alkylating agent, suitable alkylating agents may be selected from alkyl sulfonates, alkyl halides or alkyl sulfates. The alkyl group may be methyl, ethyl, propyl or isopropyl. When the alkylating agent is a halide, preferably the agent is a chloride, bromide or iodide. When the alkylating agent is a sulfonate, it is preferred to use dimethyl sulfonate or methyl aryl sulfonate. When the alkylating agent is a sulfate, the preferred sulfate is dimethyl sulfate. The preferred alkylating agent is methyl bromide, methyl iodide or salts thereof or dimethyl sulfate.

The compound of the formula (II) is reacted with the alkylating agent in an amount of suitably up to 10 equivalents, preferably from 1 to 20, especially from 5 to 10 equivalents.

The reaction between compound (II) and the alkylating agent may also be carried out in the presence of a base. Suitable bases include alkali metal hydrides, for example sodium hydride; alkali metal carbonates such as potassium carbonate or sodium carbonate or hydrogen carbonates; alkali metal alkoxides, for example sodium methoxide; and alkali metal hydroxides, for example sodium hydroxide and potassium hydroxide. Alternatively, this reaction may be carried out in the presence of an organic base such as pyridine or triethylamine; or a quaternary ammonium salt such as benzyltriethylammonium halide, for example the chloride or bromide salt or salts of $R_4NOH$, $R_4NOalkyl$, for example $Bu_4NOH$. The preferred base is potassium carbonate or potassium hydroxide.

The reaction also may be carried out in the presence of a solvent, preferably a polar organic solvent which may be selected from ethers such as tetrahydrofuran, t-butyl methyl ether, dioxane, diisopropyl ether and dibutyl ether; halogenated aromatic or aliphatic hydrocarbons such as dichloromethane, 1,2-dichloroethane and monochlorobenzene; polar nitriles and amides such as acetonitrile, N,N-dimethylformamide and N-methylpyrrolidinone. The preferred solvent is acetonitrile, N,N-dimethylformamide or N-methylpyrrolidinone. There may also be present a nonpolar solvent such as toluene. The solvent is suitably present in excess.

When the compound of the formula (II) is initially reacted with an organic base or an inorganic metal salt, the inorganic metal salt may be a Group I or II metal salt selected from cesium, potassium, sodium, calcium and magnesium. Preferably, the metal salt is a potassium or sodium metal salt. The salt may be in the aqueous or solid form and may suitably be a hydroxide, a carbonate or a hydrogen carbonate. The preferred salt for use in the process of the present invention is potassium carbonate or potassium hydroxide. The organic base is suitably an amine, for example triethylamine, pyridine and the like.

The compound of the formula (II) is reacted with the metal salt or the organic base in a ratio of at least 1 equivalent, preferably 2 equivalents.

The first step, to produce the intermediate compound, may be carried out in the presence of a solvent, preferably a polar organic solvent which may be selected from ethers such as tetrahydrofuran, t-butyl methyl ether, dioxane, diisopropyl ether and dibutyl ether; halogenated aromatic or aliphatic hydrocarbons such as dichloromethane, 1,2-dichloroethane and monochlorobenzene; polar nitriles and amides such as acetonitrile, N,N-dimethylformamide and N-methylpyrrolidinone or a mixture thereof. The preferred solvent is acetonitrile, N,N-dimethylformamide or N-methylpyrrolidinone. There may also be present a nonpolar solvent such as toluene. The solvent is suitably present in excess.

The intermediate product obtained is a novel product and herewith provides another aspect of the present invention, in particular when the compound of the formula (II) is reacted with potassium carbonate to generate the potassium salt or with triethylamine to produce the amine salt.

The intermediate compound is then reacted with an alkylating agent of the formula (III). The alkylating agent may be selected from alkyl sulfonates, alkyl halides or alkyl sulfates. The alkyl group may be methyl, ethyl, propyl or isopropyl. When the alkylating agent is a halide, preferably the agent is a chloride, bromide or iodide. When the alkylating agent is a sulfonate, it is preferred to use dimethyl sulfonate or methyl aryl sulfonate. When the alkylating agent is a sulfate, the preferred sulfate is dimethyl sulfate.

The preferred alkylating agent is methyl bromide, methyl iodide or salts thereof or dimethyl sulfate.

The ratio of alkylating agent to the intermediate metal salt is suitably up to 10 equivalents, preferably from 1 to 20, especially from 5 to 10 equivalents.

The second step of the process may also be carried out in the presence of a base. Bases suitable for use in this second step include alkali metal hydrides, for example sodium hydride; alkali metal carbonates such as potassium carbonate or sodium carbonate or hydrogen carbonates; alkali metal alkoxides, for example sodium methoxide; and alkali metal hydroxides, for example sodium hydroxide and potassium hydroxide. Alternatively, the second step may be carried out in the presence of an organic base such as pyridine or triethylamine; or a quaternary ammonium salt such as benzyltriethylammonium halide, for example the chloride or bromide salt or salts of $R_4NOH$, $R_4NOalkyl$, for example $Bu_4NOH$. The preferred base is potassium carbonate or potassium hydroxide.

The second step of the reaction also may be carried out in the presence of a solvent, preferably a polar organic solvent which may be selected from ethers such as tetrahydrofuran, t-butyl methyl ether, dioxane, diisopropyl ether and dibutyl ether; halogenated aromatic or aliphatic hydrocarbons such as dichloromethane, 1,2-dichloroethane and monochlorobenzene; polar nitrites and amides such as acetonitrile, N,N-dimethylformamide and N-methylpyrrolidinone. The preferred solvent is acetonitrile, N,N-dimethylformamide or N-methylpyrrolidinone. There may also be present a non-polar solvent such as toluene. The solvent is suitably present in excess.

The process according to the present invention may be carried out at a temperature of from 0° C. to 150° C., preferably from 20° C. to 90° C. and at atmospheric or elevated pressure.

The process of the present invention is particularly preferred for the production of a compound according to the formula (I) wherein:

$R^1$ is CN;

X is $CR_4$;

$R^2$ and $R^4$ are each chloro;

$R^3$ is trifluoromethyl;

$R^5$ is ethyl;

$R^6$ is methyl; and n is 1.

The compounds of formula (II) may be obtained by a process (B), wherein a compound of the formula (IV):

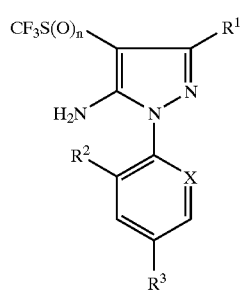

(IV)

wherein the various symbols are as defined above, is reacted with an acylating agent of formula (V) or formula (VI):

$$R^5-O\diagup\underset{O}{\overset{}{C}}\diagdown Y \qquad \text{(V)}$$

$$Z\diagup\underset{O}{\overset{}{C}}\diagdown Y \qquad \text{(VI)}$$

wherein $R^5$ is as defined above and Y is halo, especially chloro or bromo; alkoxy or anhydride, especially halo, e.g., chloro and Z is halo, for example chloro, bromo or iodo.

The preferred compound of formula (V) is the compound in which $R^5$ is ethyl and Y is chloro and for formula (VI), that wherein Z is chloro and Y is chloro.

The process (B) is preferably carried out in the presence of a solvent, preferably a polar organic solvent which may be selected from ethers such as tetrahydrofuran, t-butyl methyl ether, dioxane, diisopropyl ether and dibutyl ether; halogenated aromatic or aliphatic hydrocarbons such as dichloromethane, 1,2-dichloroethane and monochlorobenzene; polar nitrites and amides such as acetonitrile, N,N-dimethylformamide and N-methylpyrrolidinone or a mixture thereof. The preferred solvent is acetonitrile, N,N-dimethylformamide or N-methylpyrrolidinone. There may also be present a non-polar solvent such as toluene. The solvent is suitably present in excess.

The process (B) is also preferably carried out in the presence of an organic or inorganic base. Bases suitable for use in this process include alkali metal hydrides, for example sodium hydride; alkali metal carbonates such as potassium carbonate or sodium carbonate or hydrogen carbonates; alkali metal alkoxides, for example sodium methoxide; and alkali metal hydroxides, for example sodium hydroxide and potassium hydroxide. Alternatively, the reaction may be carried out in the presence of an organic base such as pyridine or triethylamine; or a quaternary ammonium salt such as benzyltriethylammonium halide, for example the chloride or bromide salt or salts of $R_4NOH$, $R_4NOalkyl$, for example $Bu_4NOH$. The preferred base is potassium hydroxide, sodium hydroxide or triethylamine. The reaction temperature is generally from minus 20° C. to 150° C., preferably from 20° C. to 90° C.

In a particular embodiment of the present invention, when compound (VI) is used to produce compound (II), and Z and Y are each chloro, this compound is reacted in the presence of a metal alkoxide, for example sodium ethoxide.

Compounds of formulas (III), (IV) and (V) and (VI) are known or may be prepared by known methods.

The intermediate salt of the compound of formula (II) may also be obtained directly from the reaction medium of a compound of formula (IV) with compound (V) as discussed above. The isolation of this salt may be carried out by filtration or by the addition of any suitable solvent.

The present invention will now be illustrated by reference to the following examples:

EXAMPLE 1

Step 1: Preparation of the potassium salt of 1-(2,6-dichloro-4-trifluoromethylphenyl)-3-cyano-4-trifluoromethylsulfinyl-5-(ethoxyacetamido)pyrazole.

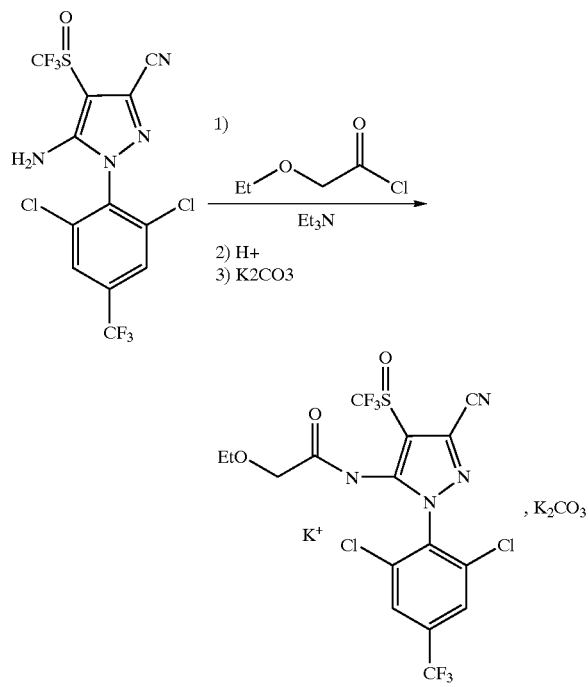

30 g of ethoxyacetyl chloride (0.233 mol) was added to a mixture of 1-(2,6-dichloro-4-trifluoromethylphenyl)-3-cyano-4-trifluoromethylsulfinyl-5-aminopyrazole (66 g, 0.145 mol) and triethylamine (44.5 g, 0.435 mol) in 100 mL of tetrahydrofuran. The reaction mixture was stirred at 30° C. during 5 hours, allowed to cool and 150 mL of water and 150 mL of $CH_2Cl_2$ were added. The pH was reduced to pH 2 with concentrated hydrochloric acid and the product extracted with $CH_2Cl_2$. A solution of potassium carbonate (50%) was added and the resulting precipitate concentrated to provide the potassium salt of the compound of formula (II). (yield=65%, assay=77%).

Step 2: Preparation of 1-(2,6-dichloro-4-trifluoromethylphenyl)-3-cyano-4-trifluoromethylsulfinyl-5-(N-methylethoxyacetamido)pyrazole.

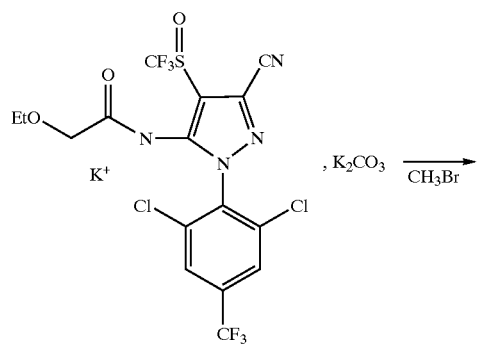

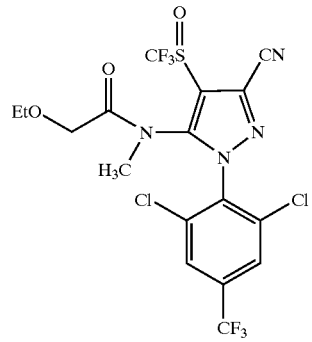

To a suspension of the potassium salt of 1-(2,6-dichloro-4-trifluoromethylphenyl)-3-cyano-4-trifluoromethylsulfinyl-5-(ethoxyacetamido)pyrazole, prepared in Step 1 above, (18.9 g, assay=75.6%, 0.026 mol) in 56.8 g of acetonitrile, a solution of methyl bromide in acetonitrile (86.5 g, conc=28%, 0.255 mol) was added. The mixture was stirred during 6 hours at 60° C. and then concentrated to dryness. The residue was solubilized in a mixture of toluene (100 g) and water (100 g). The organic layer was washed with 100 g of water and concentrated to a 38% solution, heated to 80° C. and product was recrystallized in a 40/60 toluene/n-heptane solution to afford 10.3 g of a white solid (yield=64%, assay=85%).

EXAMPLE 2

Step 1: Preparation of the TEA salt of 1-(2,6-dichloro-4-trifluoromethylphenyl)-3-cyano-4-trifluoromethylsulfinyl-5-(ethoxyacetamido)pyrazole.

3.32 g of ethoxyacetyl chloride (0.03 mol) was added to a mixture of 1-(2,6-dichloro-4-trifluoromethylphenyl)-3-cyano-4-trifluoromethylsulfinyl-5-aminopyrazole (8.74 g, 0.02 mol) and triethylamine (8.4 mL, 0.06 mol) in 20 mL of tetrahydrofuran. The reaction mixture was stirred at 60° C. during 1 hour and 1.1 g (0.01 mmol) of ethoxyacetyl chloride was added to the medium. After stirring for 30 minutes, the reaction mixture was allowed to cool and 20 mL of water and 20 mL of $CH_2Cl_2$ were added. The organic layer was washed with 10 mL of water and dried over magnesium sulfate. 12.5 g of the triethylamine salt of the compound of formula (II) was obtained, giving a yield of 90% and an assay of 76%.

Step 2: 0.42 mol of the triethylamine salt of 1-(2,6-dichloro-4-trifluoromethylphenyl)-3-cyano-4-trifluoromethylsulfinyl-5-(ethoxyacetamido)pyrazole, prepared according to step 1 above, was dissolved in 5 mL of $CH_2Cl_2$. The pH was acidified to pH 2 with concentrated hydrochloric acid and the organic layer separated. The organic layer was then treated with a concentrated solution of NaOH (1.5 equivalents) and iodomethane (1.5 equivalents) to provide a yield of 40% of the compound of formula (I).

EXAMPLE 3

Step 1: 3.1 g of ethoxyacetyl chloride (0.024 mol) was added during 2 hours to a mixture of 1-(2,6-dichloro-4-trifluoromethylphenyl)-3-cyano-4-trifluoromethylsulfinyl-5-aminopyrazole (10 g, 0.022 mol) and KOH (3.2 g, 0.57 mol) in 7 g of $CH_3CN$. The reaction mixture was stirred at −5° C. during 2 hours and the resulting mixture filtered: 15 g of the wet solid was obtained. After drying 12.2 g of the potassium salt of the compound of formula (II) was obtained (yield=87%, assay=82%).

Step 2: Preparation of 1-(2,6-dichloro-4-trifluoromethylphenyl)-3-cyano-4-trifluoromethylsulfinyl-5-N-methylethoxyacetamido)pyrazole.

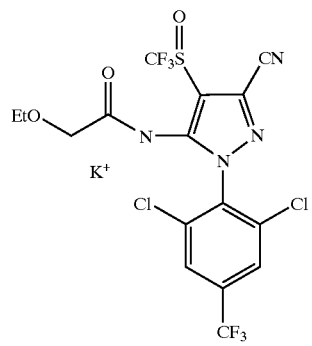

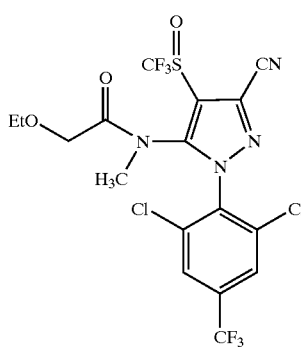

To a suspension of the potassium salt of 1-(2,6-dichloro-4-trifluoromethylphenyl)-3-cyano-4-trifluoromethylsulfinyl-5-(ethoxyacetamido)pyrazole (0.251 g, assay=82%, 0.036 mmol in 1.3 g of acetonitrile, a solution of methyl bromide in acetonitrile 0.7 g, conc=28%, 2.1 mol was added. The mixture was stirred during 6 hours at 60° C. in a pressure vessel. Chemical yield of the final compound is 85%.

EXAMPLE 4

1 equivalent of fipronil was reacted with 0.65 equivalent of ethoxyacetyl chloride in tetrahydrofuran with 3 equivalents of triethylamine and a trace of 4-dimethylaminopyridine to provide a 75% yield based on the acetyl chloride of 1-(2,6-dichloro-4-trifluoromethylphenyl)-3-cyano-4-trifluoromethylsulfinyl-5-(ethoxyacetamido)pyrazole.

The product was then treated with a 1:1 equivalent of dimethyl sulfate and a 1:1 equivalent of potassium carbonate in tetrahydrofuran at 25° C. for 4 hours to provide 1-(2,-6-dichloro-4-trifluoromethylphenyl)-3-cyano-4-trifluoromethylsulfinyl-5-(N-methylethoxyacetamido)pyrazole.

What is claimed is:

1. A process for the preparation of a compound of the formula (I):

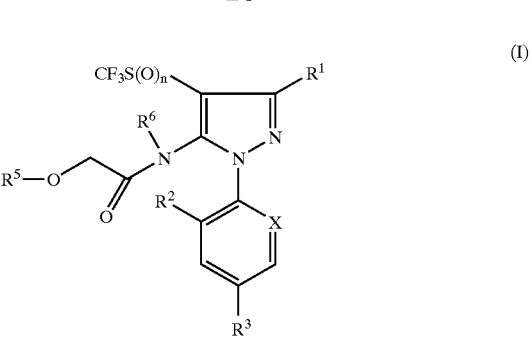

wherein:
- $R^1$ is CN or $CSNH_2$;
- X is N or $CR^4$;
- $R^2$ and $R^4$ are each independently hydrogen or chloro;
- $R^3$ is halo, haloalkyl, haloalkoxy or $-SF_5$;
- $R^5$ and $R^6$ are each independently alkyl; and
- n is 0, 1 or 2;

said process comprising:
(a) in a first step, reacting a compound of the formula (II):

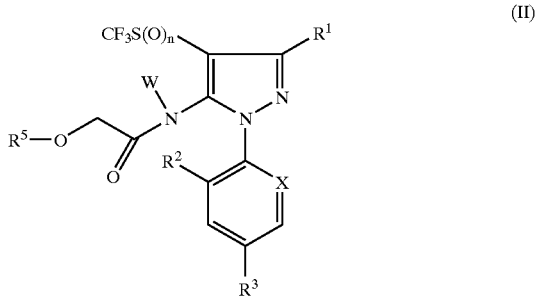

wherein $R^1$, $R^2$, $R^3$, X, $R^5$ and n are as defined above and W is H, with an inorganic metal salt or an organic base, to afford, as an intermediate, a salt of said compound of formula (II); and (b) in a second step, reacting said salt of said compound of formula (II) with an alkylating agent of the formula (III):

wherein $R^6$ is as defined above and Y is a leaving group.

2. A process for the preparation of a compound of the formula (I):

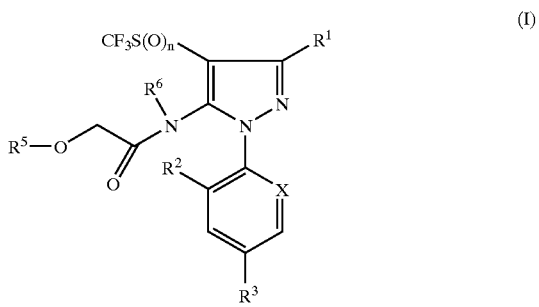

wherein:

$R^1$ is CN or $CSNH_2$;

X is N or $CR^4$;

$R^2$ and $R^4$ are each independently hydrogen or chloro;

$R^3$ is halo, haloalkyl, haloalkoxy or $-SF_5$;

$R^5$ and $R^6$ are each independently alkyl; and n is 0, 1 or 2;

said process comprising reacting an inorganic metal or organic salt of a compound of the formula (II)

$$CF_3S(O)_n \quad R^1 \quad (II)$$

(structure with pyrazole ring, W, N, N, $R^2$, phenyl with X and $R^3$, and $R^5-O-CH_2-C(=O)-$ group)

wherein $R^1$, $R^2$, $R^3$, X, $R^5$ and n are as defined above and W is H, with an alkylating agent of the formula (III)

$$R^6-Y \quad (III)$$

wherein $R^6$ is as defined above and Y is a leaving group.

3. A process as claimed in claim 2, wherein the alkylating agent is an alkyl halide, an alkyl sulfonate or an alkyl sulfate.

4. A process as claimed in claim 1, wherein the alkylating agent is an alkyl halide, an alkyl sulfonate or an alkyl sulfate.

5. A process as claimed in claim 3, wherein the alkylating agent is methyl bromide, methyl iodide or dimethyl sulfonate.

6. A process as claimed in claim 4, wherein the alkylating agent is methyl bromide, methyl iodide or dimethyl sulfonate.

7. A process as claimed in claim 2, said process being conducted in the presence of a solvent.

8. A process as claimed in claim 1, said process being conducted in the presence of a solvent.

9. A process as claimed in claim 1, said process being conducted in the presence of a solvent.

10. A process as claimed in claim 4, said process being conducted in the presence of a solvent.

11. A process as claimed in claim 1, wherein the first and second steps are conducted in the presence of a base.

12. A process as claimed in claim 3, conducted in the presence of a base.

13. A process as claimed in claim 6, wherein said first and second steps are conducted in the presence of a base.

14. A process as claimed in claim 7, conducted in the presence of a base.

15. A process as claimed in claim 1, wherein the inorganic metal salt is a salt of a Group I or Group II metal selected from the group consisting of cesium, potassium, sodium, magnesium and calcium.

16. A process as claimed in claim 3, wherein the inorganic metal salt of the compound of formula (II) is a salt of a Group I or Group II metal selected from the group consisting of cesium, potassium, sodium, magnesium and calcium.

17. A process as claimed in claim 6, wherein the inorganic metal salt is a salt of a Group I or Group II metal selected from the group consisting of cesium, potassium, sodium, magnesium and calcium.

18. A process as claimed in claim 7, wherein the inorganic metal salt of the compound formula (II) is a salt of a Group I or Group II metal selected from the group consisting of cesium, potassium, sodium, magnesium and calcium.

19. A process as claimed in claim 11, wherein the inorganic metal salt is a salt of a Group I or Group II metal selected from the group consisting of cesium, potassium, sodium, magnesium and calcium.

20. A process as claimed in claim 15, wherein the inorganic metal salt is a hydroxide, a carbonate or a hydrogen carbonate.

21. A process as claimed in claim 16, wherein the inorganic metal salt is a hydroxide, a carbonate or a hydrogen carbonate.

22. A process as claimed in claim 15, wherein the inorganic metal salt is potassium carbonate or potassium hydroxide.

23. A process as claimed in claim 16, wherein the inorganic metal salt is potassium carbonate or potassium hydroxide.

24. A process as claimed in claim 17, wherein the inorganic metal salt is potassium carbonate or potassium hydroxide.

25. A process as claimed in claim 18, wherein the inorganic metal salt is potassium carbonate or potassium hydroxide.

26. A process as claimed in claim 19, wherein the inorganic metal salt is potassium carbonate or potassium hydroxide.

27. A process as claimed in claim 1, wherein the organic base is triethylamine or pyridine.

28. A process as claimed in claim 3, wherein the organic salt of the compound of formula (II) is a salt of triethylamine or pyridine.

29. A process as claimed in claim 6, wherein the organic base is triethylamine or pyridine.

30. A process as claim in claim 1, wherein the compound of formula (II) is reacted with the inorganic metal salt or the organic base in a ratio of at least one equivalent.

31. A process as claimed in claim 30, wherein the compound of formula (II) is reacted with the inorganic metal salt or the organic base in a ratio of 2 equivalents.

32. A process as claimed in claim 2, wherein, in the compound of formula (II), $R^1$ is CN, X is $CR^4$, $R^2$ and $R^4$ are each chloro, $R^3$ is trifluoromethyl, $R^5$ is ethyl and n is 1.

33. A process as claimed in claim 1, wherein, in the compound of formula (II), $R^1$ is CN, X is $CR^4$, $R^2$ and $R^4$ are each chloro, $R^3$ is trifluoromethyl, $R^5$ is ethyl and n is 1.

34. A process as claimed in claim 1, comprising:

(a) in a first step, reacting 1-(2,6-dichloro-4-trifluoromethylphenyl)-3-cyano-4-trifluoromethyl-sulfinyl-5-(ethoxyacetamido)pyrazole with potassium carbonate to afford the potassium salt of 1-(2,6-dichloro-4-trifluoromethylphenyl)-3-cyano-4-trifluoromethylsulfinyl-5-(ethoxyacetamido)pyrazole; and (b) in a second step, reacting the resultant potassium salt with methyl bromide to afford 1-(2,6 dichloro-4-trifluoromethylphenyl)-3-cyano-4-trifluoromethyl-sulfinyl-5-(N-methylethoxyacetamido)pyrazole.

35. A process as claimed in claim 1, comprising:

(a) in a first step, reacting 1-(2,6-dichloro-4-trifluoromethylphenyl)-3-cyano-4-trifluoromethyl-sulfinyl-5-(ethoxyacetamido)pyrazole with triethylamine to afford the triethylamine salt of 1-(2,6- dichloro-4-trifluoromethylphenyl)-3-cyano-4-trifluoromethylsulfinyl-5-(ethoxyacetamido)pyrazole; and (b) in a second step, reacting the resulting triethylamine salt with iodomethane to afford 1-(2,6-dichloro-4-trifluoromethylphenyl)-3-cyano-4-trifluoromethyl-sulfinyl-5-(N-methylethoxyacetamido)pyrazole.

36. A process as claimed in claim 2, comprising reacting the potassium salt of 1-(2,6-dichloro-4-trifluoromethylphenyl)-3-cyano-4-trifluoromethylsulfinyl-5-(ethoxyacetamido)pyrazo with methyl bromide to afford 1-(2,6-dichloro-4-trifluoromethylphenyl)-3-cyano-4-trifluoromethylsulfinyl-5-(N-methylethoxyacetamido)pyrazole.

37. A process as claimed in claim 2, comprising reacting the triethylamine salt of 1-(2,6-dichloro-4-trifluoromethylphenyl)-3-cyano-4-trifluoromethylsulfinyl-5-(ethoxyacetamido)pyrazole with iodomethane to afford 1-(2,6-dichloro-4-trifluoromethylphenyl)-3-cyano-4-trifluoromethyl-5-(N-methyloxyacetamido)pyrazole.

* * * * *